US00PP16971P3

(12) United States Plant Patent
Jamieson

(10) Patent No.: US PP16,971 P3
(45) Date of Patent: Aug. 8, 2006

(54) STRAWBERRY VARIETY NAMED 'CABOT'

(50) Latin Name: *Fragaria ananassa*
Varietal Denomination: Cabot

(75) Inventor: Andrew R. Jamieson, Nova Scotia (CA)

(73) Assignee: Her Majesty the Queen in Right of Canada, as represented by the Minister of Agriculture and Agrifood, Atlantic Food and Horticulture Research Centre, Agriculture and Agri-Food Canada, Nova Scotia (CA)

( * ) Notice: Subject to any disclaimer, the term of this patent is extended or adjusted under 35 U.S.C. 154(b) by 89 days.

(21) Appl. No.: 10/755,842

(22) Filed: Jan. 12, 2004

(65) Prior Publication Data

US 2005/0160507 P1 Jul. 21, 2005

Related U.S. Application Data

(63) Continuation of application No. 10/073,446, filed on Feb. 11, 2002, now abandoned.

(51) Int. Cl.
*A01H 5/00* (2006.01)

(52) U.S. Cl. ..... Plt./208

(58) Field of Classification Search ..... Plt./208, Plt./209
See application file for complete search history.

(56) References Cited

PUBLICATIONS

GTITM UPOVROM Citation for 'Cabot' as per CA PBR 97–998; Mar. 13, 1997.*

* cited by examiner

*Primary Examiner*—Kent Bell
(74) *Attorney, Agent, or Firm*—The Webb Law Firm

(57) ABSTRACT

This invention relates to a new and distinct variety of strawberry (*Fragaria ananassa*) named 'Cabot' characterized by its few, small flowers, large calyx, large and light colored fruit, and resistance to red stele root. The invention is distinct from other varieties, but most similar to 'Bounty'.

3 Drawing Sheets

Botanical classification: *Fragaria ananassa.*
Varietal denomination: 'Cabot'.

BACKGROUND OF THE INVENTION

The present invention includes a new and distinct cultivar of *Fragaria ananassa* known by the varietal name 'Cabot', originally designated as "K92-17". The new variety resulted from a controlled cross in an ongoing breeding program between the strawberry plants 'K87-5' (female parent) and 'K86-19' (male parent). Both parents are unpatented varieties developed in Kentville. 'Cabot' was discovered in 1992 as a seedling in a controlled breeding plot near Sheffield Mills, Nova Scotia, in a field-station, where it was selected and propagated asexually by stolons in Kentville. Asexual propagules from this original source have been produced annually in a greenhouse in Kentville, Canada. 'Cabot' has been tested in Kentville, Canada (starting in 1993) and also, research centres at Charlottetown, Prince Edward Island, Buctouche, New Brunswick, Fredericton, New Brunswick, and Pynn's Brook, Newfoundland, all of Canada. This propagation and testing has demonstrated that the combination of all traits disclosed herein which characterize the new variety are fixed and retained true to type through successive generations of asexual reproduction via stolons.

DESCRIPTION OF THE PLANT

Figure 1:
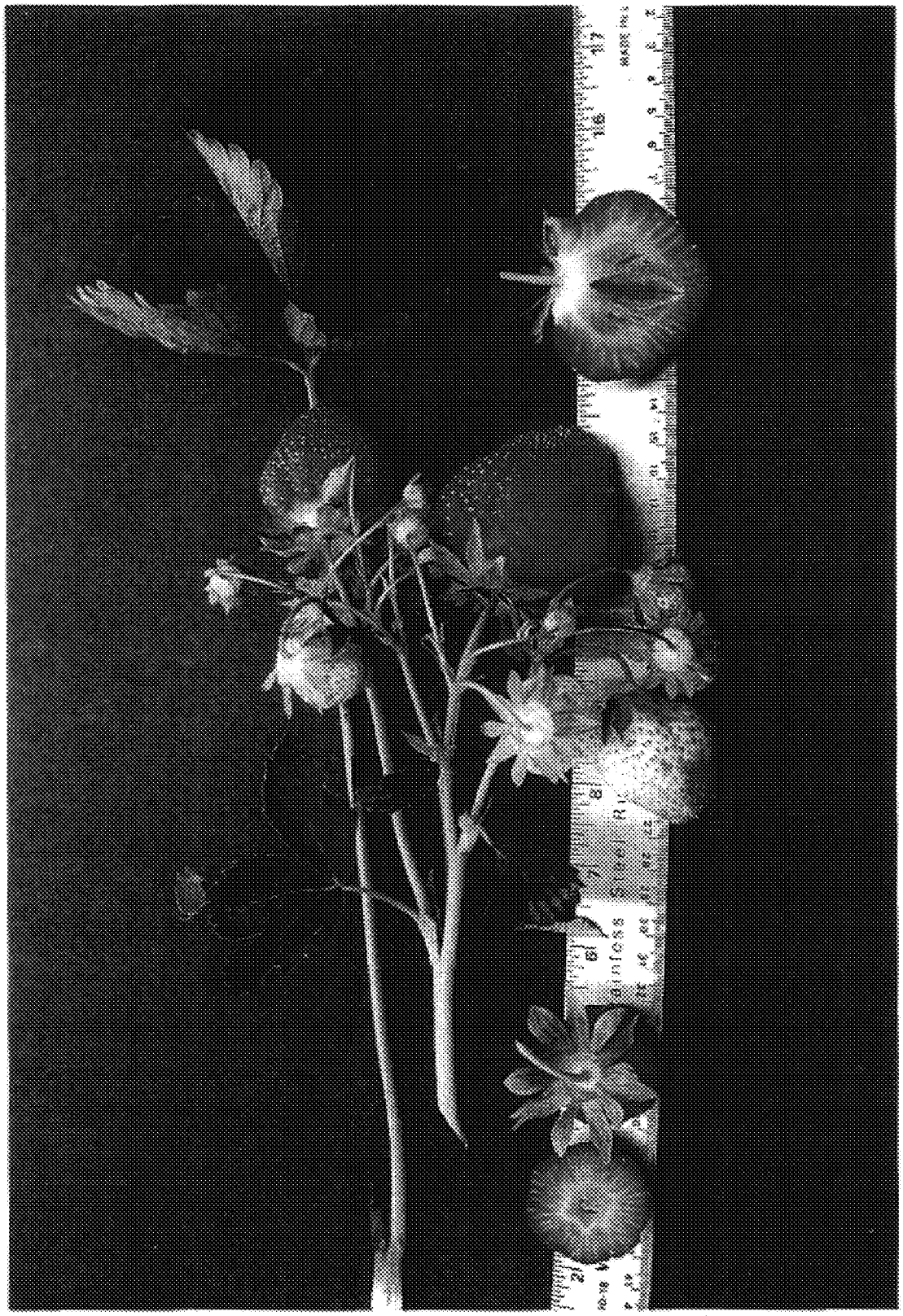
FIG. 1 shows plant parts of the new variety, typical in size, shape, and color.
Figure 2:
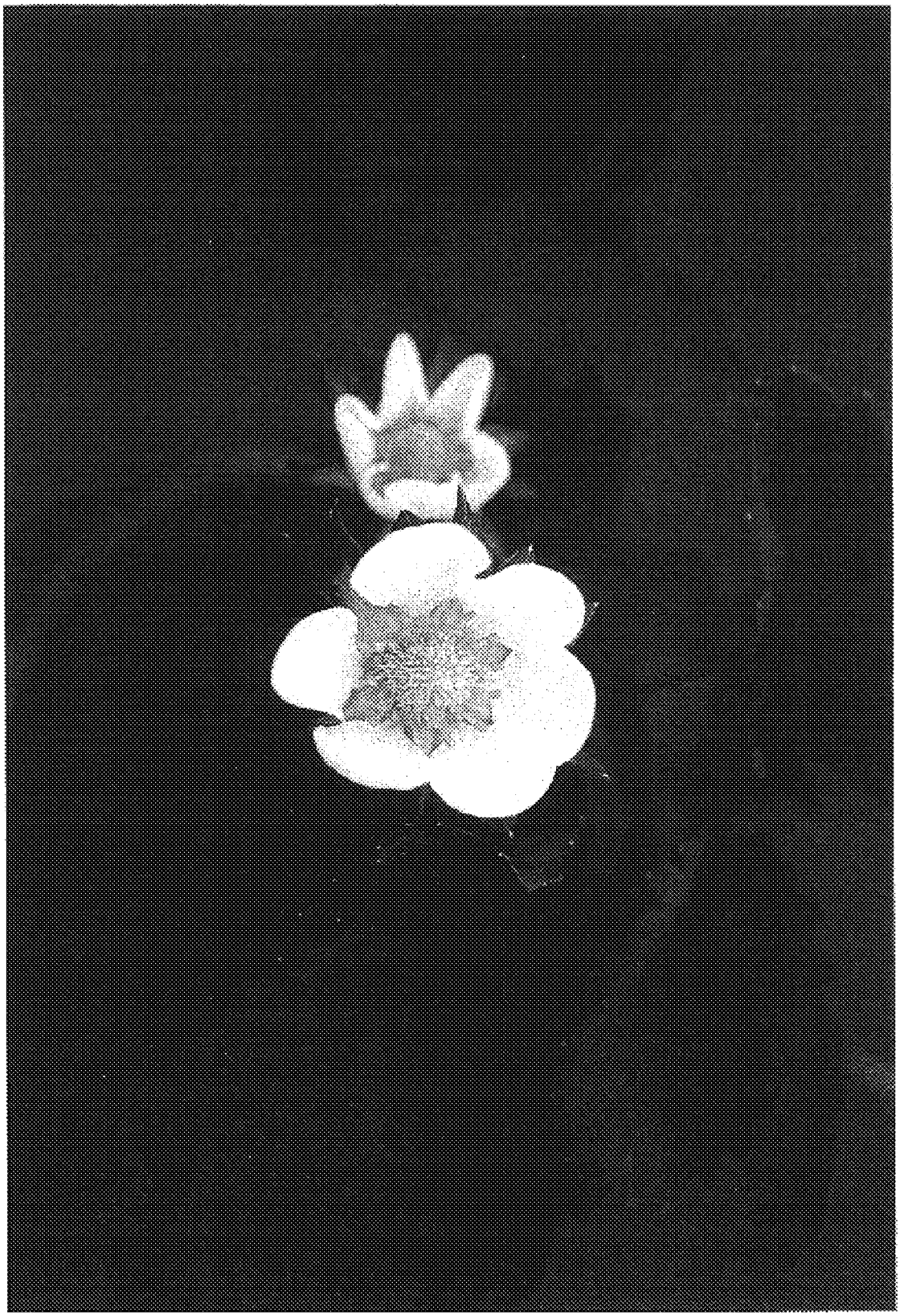
FIG. 2 shows the flowers of the new variety.
Figure 3:
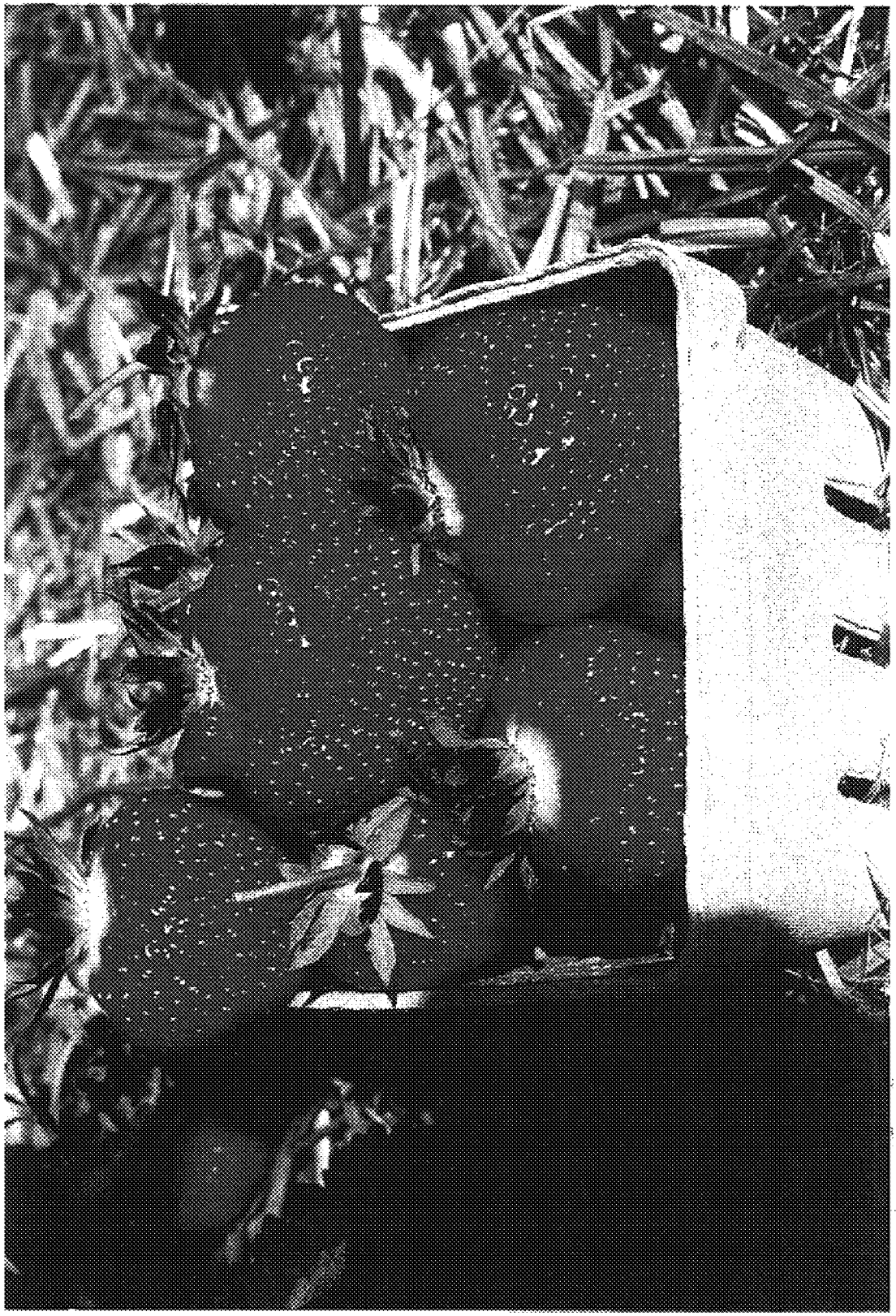
FIG. 3 shows primary fruit of the new variety in a quart box.

The following detailed botanical description of the new variety is based upon measurements and observations taken of plants and fruit grown in Kentville, Nova Scotia, Canada. Observations were taken from each variety as grown in a side-by-side field trial. Color designations, color descriptions, and other phenotypical descriptions may deviate from the stated values and description depending upon variation in the environment, seasonal, climatic and cultural conditions, however, it is believed that this description will apply to the 'Cabot' plants grown in similar conditions of soil and climate elsewhere. Color references are generally made to The R.H.S. Colour Chart of The Royal Horticultural Society of London (1966 edition). Descriptive information on the new variety is presented in Tables 1 and 2. In the tables, the flowers described are secondary flowers. The fruit described is the secondary fruit of the maiden crop, thirteen or fourteen months after planting. The harvest data in Table 3 is based on a complete harvest of the crop. Principal differences between 'Cabot' and the unpatented variety 'Bounty' are set forth.

Classification: The new variety is botanically identified as *Fragaria ananassa* and commercially classified as a short-day strawberry.

Plant and foliage: When propagated in the nursery, 'Cabot' produces low to medium numbers of runner plants, about half the runners of 'Bounty'. Individual plants of 'Cabot' are large. The plants of 'Cabot' are of medium to high density with globose habit and strong vigor. As shown in Table 1, leaf color of 'Cabot' and 'Bounty' are Green Group 137A on the upper surface and lighter Green Group 137C on the under surface. Leaflets of 'Cabot' and 'Bounty' are about the same size and leaves of both varieties have three leaflets. 'Cabot' leaflets are cupped whereas 'Bounty' leaflets are flat. 'Bounty' leaflets have moderate numbers of obtuse to rounded serrations, as does 'Bounty'. The tip serration on 'Cabot' leaflets is smaller than on 'Bounty'. The venation of 'Cabot' leaflets is pinnate. Leaf and petiole pubescence for 'Cabot' and 'Bounty' are similar in density.

TABLE 1

Foliar Characteristics for 'Cabot' and 'Bounty'

| Foliar character | Cultivar 'Cabot' | Cultivar 'Bounty' |
|---|---|---|
| Leaf color | Green Group | Green Group |
| Upper surface | 137A | 137A |
| Lower surface | 137C | near 137C |
| Central leaflet | | |
| Length (mm) | | |
| Mean | 73.0 | 72.9 |
| Range | 63–89 | 65–80 |
| Width (mm) | | |
| Mean | 69.3 | 68.6 |
| Range | 60–83 | 59–82 |
| Length/width ratio | 1.05 | 1.06 |
| No. leaflets/leaf | 3 | 3 |
| Leaf convexity | cupped | flat |
| Serrations | | |
| Number | moderate | moderate |
| Size | medium | medium |
| Shape | obtuse to rounded | obtuse to rounded |
| Tip serration size | small | medium |
| Leaf pubescence | medium | medium |
| Petiole pubescence | | |
| Density | sparse to medium | sparse |
| Direction | perpendicular | perpendicular |

Flower and fruit production characteristics: The length of bloom for 'Cabot' is about three weeks when grown in Kentville, Nova Scotia, Canada in a matted row cultural system. Flowering for 'Cabot' typically begins on June 1 and ends on June 21. 'Bounty' blooms later, typically beginning on June 5 and ending by June 26. As shown in Table 2, the flower truss of 'Cabot' is shorter than for 'Bounty' and opens lower in relation to the canopy. 'Cabot' flower trusses produce fewer flowers than does 'Bounty'. Flowers of 'Cabot' and the reference variety are white. The anther color is Yellow-Orange Group 17A. Secondary flowers of 'Cabot' are similar to 'Bounty' in size. Secondary flowers of 'Cabot' have 5, 6 or 7 petals while 'Bounty' has 5 or 6 petals. The inner calyx of 'Cabot' has a distinctively larger diameter than the outer calyx of 'Bounty'; the inner calyx is smaller than the outer calyx. Trusses of 'Cabot' are either semi-erect or prostrate at first picking. The position of the calyx is even with the top of the berry to slightly raised for 'Cabot' and even with the top of the berry for 'Bounty'. The calyx is easily separated from the fruit for 'Bounty' but more difficult for 'Cabot'. The fruit of 'Cabot' are much larger than for 'Bounty'. The ratio of fruit length to width is 1.02 for 'Cabot' and 0.84 for 'Bounty'. 'Cabot' fruit are conic and the larger berries may have a rough appearance with bumps of the shoulders. Fruit of 'Cabot' are firmer than 'Bounty'. As shown in Table 2, the fruit color of 'Cabot' is lighter, both externally and internally, than for 'Bounty'. The achenes of 'Cabot' are Green-Yellow Group 1A but darken to Orange-Red Group 34A on the shoulders of the fruit when exposed to sunlight. The larger berries of 'Cabot' may be hollow.

TABLE 2

Flower and Fruit Characteristics for 'Cabot' and 'Bounty'

| Character | Cultivar 'Cabot' | Cultivar 'Bounty' |
|---|---|---|
| Flower position (relative to leaf canopy) | even | above |
| Flower truss length | short–medium (21.6 cm) | medium–long (24.8 cm) |
| Number of flowers/truss | 7.3 | 14.8 |
| Number of petals | 6.0 | 5.6 |
| Flower size (mm diameter) | 29.4 | 30.7 |
| Flower color | White | White |
| Petal length (mm) | 11.6 | 11.8 |
| Petal width (mm) | 10.7 | 12.0 |
| Petal spacing | spaced to slightly overlapping | spaced to overlapping |
| Calyx size | | |
| Inner calyx (mm diam.) | 28.8 | 26.6 |
| Outer calyx (mm diam.) | 24.0 | 29.9 |
| Calyx position | even to slightly above | even |
| Adherence of the calyx | medium to strong | weak |
| Fruit Size | | |
| Length (mm) | 37.5 | 23.8 |
| Width (mm) | 36.6 | 28.2 |
| Fruit shape | | |
| Length/width ratio | 1.02 | 0.84 |
| Subjective | conic | short-conic |
| Seed position | even | even |
| Fruit firmness | medium to firm | soft |
| Skin toughness | medium | medium |
| Color (R.H.S. Colour Chart) | | |
| Calyx | Green Group. near 137C | Green Group 137D |
| Fruit exterior | Red Group near 46B | Red Group near 46A |
| Fruit interior | | |
| Pith | Red Group 43C | Red Group near 45A |
| Cortex | Red Group 42B | Red Group near 45A |

Disease resistance: 'Cabot' is resistant to red stele root (*Phytophthora fragariae*) while 'Bounty' is susceptible. 'Cabot' and 'Bounty' are moderately resistant to powdery mildew (*Sphaerotheca macularis*). 'Cabot' is rated as susceptible to fruit rot (*Botrytis cinerea*) whereas 'Bounty' is moderately susceptible.

Production characteristics: 'Cabot' has produced high yields, generally higher than 'Bounty', as shown in Table 3. In years when fruit rot has been a problem, 'Cabot' has had more unmarketable fruit than 'Bounty'. The fruit of 'Cabot' are much larger than 'Bounty'. The mean harvest date for 'Cabot' is about three days earlier than for 'Bounty'.

TABLE 3

| | Performance of 'Cabot' and 'Bounty' in 1996 and 1997 at Kentville, Nova Scotia.* | | | |
|---|---|---|---|---|
| | Total yield (t/ha) | % yield marketable | Size (g/fruit) | Mean harvest (day of year) |
| 1996 | | | | |
| 'Cabot' | 33.8 | 77.6 | 23.4 | 194.3 |

TABLE 3-continued

| | Performance of 'Cabot' and 'Bounty' in 1996 and 1997 at Kentville, Nova Scotia.* | | | |
|---|---|---|---|---|
| | Total yield (t/ha) | % yield marketable | Size (g/fruit) | Mean harvest (day of year) |
| 'Bounty' | 27.4 | 90.1 | 10.4 | 197.2 |
| 1997 | | | | |
| 'Cabot' | 23.7 | 94.3 | 17.0 | 197.5 |
| 'Bounty' | 20.9 | 92.2 | 8.7 | 200.5 |

*Plants were grown in matted rows and four blocks of 3 m long rows were harvested each year.

I claim:

1. The new and distinct variety of strawberry plant named 'Cabot' as described and illustrated.

* * * * *